United States Patent [19]

Holtkamp

[11] Plant 4,267

[45] Jun. 20, 1978

[54] AFRICAN VIOLET PLANT

[76] Inventor: Reinhold Holtkamp, Wertherstrasse 112, 4294 Isselburg, Germany

[21] Appl. No.: 774,226

[22] Filed: Mar. 3, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet cultivar characterized by medium pink flowers carried on strong, upright stems, with 6 to 10 flowers on each stem, vigorous growth, dark green leaves and long blooming period.

1 Drawing Figure

1

The present invention comprises a new and distinct cultivar of African violet plant, botanically known as *Saintpaulia ionantha,* and hereinafter referred to by the cultivar name Georgia. The new cultivar, referred to during the breeding and selection process by No. 6.40/3 - 50/76, is a product of a planned breeding program which had the objective of creating a new African violet cultivar having vigorous growth, strong upright flower stems, medium size pink flowers, and dark green and shiny leaves. These traits in combination were not present in previously available commercial cultivars.

The new cultivar was originated from a cross made in a controlled breeding program in Isselburg, Rhineland, Germany. The female, or seed parent was No. XIX 4001 red, color 45-13. The male, or pollen parent was No. XIX 4236 bordeaux red, color between 45-11 and 45-12.

The new cultivar Georgia was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The traits described below have been repeatedly observed and are determined to be basic characteristics of Georgia which in combination distinguish this African violet as a new and distinct cultivar.

1. Vigorous growth.
2. Upright and strong flower stems, with 6–10 medium size pink flowers on each stem.
3. Strong upright peduncle.
4. Long blooming period.
5. Attractive salable plant with the first flash of flowers.
6. Dark green shiny leaves.

The accompanying photographic drawing shows a typical specimen plant of the new cultivar, with the colors appearing in the photograph being as true as possible with color illustrations of this type.

In the following description, color references are made to the Munsell Color Cascade chart, except where general color terms are referred to.

2

Botanical classification: *Saintpaulia ionantha,* Ramat. cv. Georgia.

Parentage:

*Male parent.*—XIX 4236 bordeaux red.

*Female parent.*—XIX 4001 red.

Propagation: The new cultivar holds its distinguishing characteristics through successive propagations by leaf cuttings and by division of shoots.

Plant: From 10 cm. to 12 cm. tall when grown in pots, and approximately 25–30 cm. in diameter when fully grown.

Leaves:

*General form.*—Heart-shaped.

*Diameter.*—65–70 mm. when fully developed.

*Texture.*—Soft.

*Aspect.*—Shiny.

*Veins.*—Underside pronounced, on young leaves reddish to purple, older leaves turning to light green.

*Color (upperside).*—21–16.

*Color (underside).*—Older leaves light green except in veined areas.

*Petiole.*—On young leaves, reddish, when older changing to medium green.

Flowers:

*Buds.*—Globular, 8 mm. in diameter before opening, outside color before opening violet to pink.

*Sepals.*—Color: 23-14. Calyx: Funnel-shaped. Aspect: Spear-shaped. Peduncle: Brown from stem to calyx.

Individual flowers:

*Size.*—40–45 mm., mostly flat.

*Color.*—Upperside: 44-5. Underside: 44-3.

*Borne.*—Peduncle strong and upright, approximately 2 cm. long on strong and upright stem; every flower stem carries 6–10 flowers.

*Shape.*—Five petals, 2 small and 3 large.

*Corolla.*—The large petals measured from the center of the flower are 22–25 mm. long, the small petals 12–15 mm. long.

*Flowering time.*—Within 7–8 weeks after potting a saleable plant exists having 7–9 flower stems.

Reproductive organs:

*Anthers.*—Two with four cells, golden yellow 26-5.

*Filaments.*—3–4 mm. long, light yellow.

*Styles.*—7 mm. long color 44-5, stigma is good, visible white; capsule pushed slightly through.

*Pollen color.*—25-1.

Roots: Well developed, white when young and active.

Disease resistance: Good as experienced to date.

General observations: The variety Georgia is a vigorous grower and comes very uniformly in bloom. With the first flash of flowers there are between 7–10 flower stems and each carries 6–10 flowers. The flowers form a nice head and a beautiful saleable plant. The flowers do not drop after withering, and the flowerhead is free above the leaves.

I claim:

1. A new and distinct cultivar of African violet known by the cultivar name Georgia and particularly characterized as to uniqueness by the combined characteristics of vigorous growth, upright and strong flower stems each carrying 6–10 medium pink size flowers which are non-dropping; strong upright peduncle; long blooming period; dark green shiny leaves, and by the characteristic of being an attractive, saleable plant with the first flash of flowers.

* * * * *

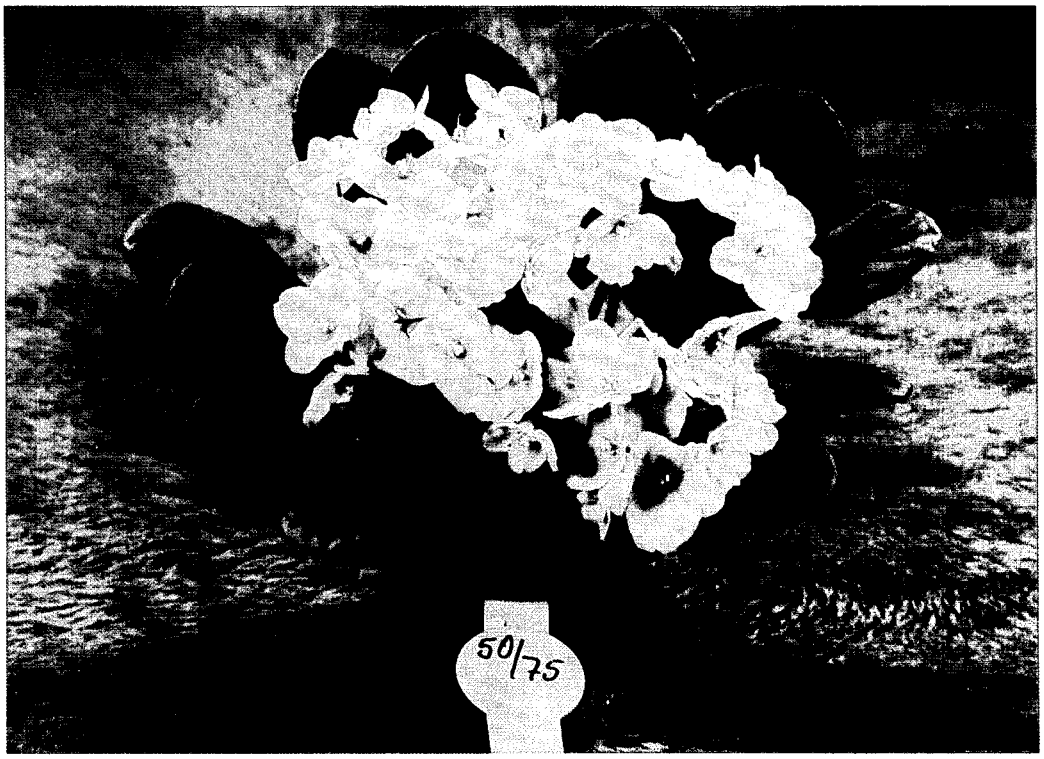
50/75